United States Patent
Kawaguchi et al.

(10) Patent No.: US 9,393,553 B2
(45) Date of Patent: Jul. 19, 2016

(54) CATALYST FOR PRODUCING UNSATURATED ALDEHYDE AND/OR UNSATURATED CARBOXYLIC ACID, METHOD FOR PRODUCING THE CATALYST, AND METHOD FOR PRODUCING UNSATURATED ALDEHYDE AND/OR UNSATURATED CARBOXYLIC ACID USING THE CATALYST

(71) Applicant: Nippon Kayaku Kabushiki Kaisha, Tokyo (JP)

(72) Inventors: Toru Kawaguchi, Yamaguchi (JP); Yoshiko Shoya, Yamaguchi (JP); Asa Taniguchi, Yamaguchi (JP); Masashi Hashiba, Gunma (JP); Hideo Yoshida, Yamaguchi (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/785,714

(22) PCT Filed: Apr. 15, 2014

(86) PCT No.: PCT/JP2014/060676
§ 371 (c)(1),
(2) Date: Oct. 20, 2015

(87) PCT Pub. No.: WO2014/175113
PCT Pub. Date: Oct. 30, 2014

(65) Prior Publication Data
US 2016/0059220 A1 Mar. 3, 2016

(30) Foreign Application Priority Data
Apr. 25, 2013 (JP) ................................. 2013-092005

(51) Int. Cl.
| | | |
|---|---|---|
| *B01J 23/652* | (2006.01) | |
| *C07C 45/35* | (2006.01) | |
| *C07C 51/215* | (2006.01) | |
| *B01J 23/89* | (2006.01) | |
| *B01J 23/887* | (2006.01) | |
| *B01J 35/02* | (2006.01) | |
| *B01J 23/00* | (2006.01) | |
| *C07C 51/25* | (2006.01) | |
| *B01J 37/04* | (2006.01) | |
| *B01J 37/08* | (2006.01) | |

(52) U.S. Cl.
CPC ............ *B01J 23/8993* (2013.01); *B01J 23/002* (2013.01); *B01J 23/8876* (2013.01); *B01J 35/023* (2013.01); *C07C 45/35* (2013.01); *C07C 51/215* (2013.01); *C07C 51/252* (2013.01); *B01J 37/04* (2013.01); *B01J 37/08* (2013.01); *B01J 2523/00* (2013.01)

(58) Field of Classification Search
CPC .......... C07C 45/35; C07C 47/22; B01J 23/88; B01J 35/002; B01J 37/08
See application file for complete search history.

(56) References Cited

U.S. PATENT DOCUMENTS

| | | | |
|---|---|---|---|
| 5,532,199 | A | 7/1996 | Watanabe et al. |
| 6,399,818 | B2 | 6/2002 | Tanimoto et al. |
| 6,784,134 | B2 | 8/2004 | Kasuga et al. |
| 2002/0007088 | A1 | 1/2002 | Tanimoto et al. |
| 2002/0198103 | A1 | 12/2002 | Kasuga et al. |
| 2013/0172615 | A1 | 7/2013 | Kawano et al. |

FOREIGN PATENT DOCUMENTS

| | | | |
|---|---|---|---|
| JP | 6-381 | A | 1/1994 |
| JP | 06-000381 | A * | 1/1994 |
| JP | 9-52053 | A | 2/1997 |
| JP | 2001-328951 | A | 11/2001 |
| JP | 2002-273229 | A | 9/2002 |
| JP | 2007-803 | A | 1/2007 |
| JP | 2008-68228 | A | 3/2008 |
| JP | 2011-177616 | A | 9/2011 |
| WO | 2012/036038 | A1 | 3/2012 |

OTHER PUBLICATIONS

International Search Report mailed Jul. 22, 2014 in corresponding PCT application No. PCT/JP2014/060676.

* cited by examiner

*Primary Examiner* — Paul A Zucker
(74) *Attorney, Agent, or Firm* — Nields, Lemack & Frame, LLC

(57) ABSTRACT

An object of the invention is to provide a novel catalyst having high mechanical strength and capable of obtaining an unsaturated aldehyde or an unsaturated carboxylic acid in a high yield and a method for producing the same, and a method for producing an unsaturated aldehyde and/or an unsaturated carboxylic acid using the catalyst. By containing silane-treated glass fibers in a catalytic active component composed of molybdenum and bismuth as essential components, high mechanical strength is revealed, and it is possible to obtain an unsaturated aldehyde or an unsaturated carboxylic acid in a high yield.

7 Claims, No Drawings

CATALYST FOR PRODUCING UNSATURATED ALDEHYDE AND/OR UNSATURATED CARBOXYLIC ACID, METHOD FOR PRODUCING THE CATALYST, AND METHOD FOR PRODUCING UNSATURATED ALDEHYDE AND/OR UNSATURATED CARBOXYLIC ACID USING THE CATALYST

TECHNICAL FIELD

The present invention relates to a novel catalyst for producing an unsaturated aldehyde and/or an unsaturated carboxylic acid, a method for producing the catalyst, and a method for producing an unsaturated aldehyde and/or an unsaturated carboxylic acid using the catalyst.

BACKGROUND ART

Methods in which propylene, isobutylene or tertiary butyl alcohol is used as a raw material to produce a corresponding unsaturated aldehyde or unsaturated carboxylic acid are industrially widely carried out. However, the generation of a local high-temperature portion (hot spot) in a catalyst layer is a significant problem. The generation of a hot spot leads to shortening of a catalyst service life or lowering of a yield to be caused due to an excessive oxidation reaction, and in the worst case, the generation of an accident hazard due to a runaway reaction or out of order of a catalyst, and therefore, technologies for suppressing the hot spot are proposed. For example, Patent Document 1 discloses a technology of using a shaped catalyst whose activity is regulated by varying an occupation volume of the catalyst or a calcining temperature of the catalyst.

Among such catalysts, with respect to those having a large average particle diameter and/or those having a high calcining temperature, the catalyst layer becomes thick, and therefore, there may be the case where a strain in the catalytic active component layer is generated, or the mechanical strength is lowered due to a crystal phase change at the time of calcination, and there is a concern about the generation of such a problem that during the storage of a completed catalyst, the catalyst in a storage container bottom is broken, or at the time of filling in a reaction tube, the catalyst is broken, resulting in an increase of pressure loss of the reaction tube. Above all, such a tendency is more likely seen in catalysts having not only a large average particle diameter but also a high calcining temperature, and the production efficiency of the catalyst is remarkably lowered, and hence, improvements are considered to be needed. It is to be noted that the calcining temperature as referred to herein indicates a maximum temperature in a calcining step to be carried out for the purpose of imparting activity to the catalyst, and typically, it means a maximum temperature of the temperature of calcining or drying to be carried out for the catalytic active component.

As a method of enhancing the strength of a catalyst, Patent Document 2 discloses a shaped catalyst by containing inorganic fibers in a ring-formed shaped catalyst containing molybdenum and bismuth. In addition, Patent Document 2 discloses that at least one member selected from glass fibers, aluminum fibers and silica fibers, each having an average fiber length of 50 μm to 1.5 mm and an average diameter of 2 μm to 20 μm, can be used as the inorganic fibers. However, though the mechanical strength is improved to some extent by adding such a shaping auxiliary agent, the yield of the target unsaturated aldehyde or unsaturated carboxylic acid is not sufficient yet, and catalysts having both mechanical strength and catalytic performances (for example, activity, yield, etc.) are considered to be needed.

Patent Document 3 discloses a method of using, as a carrier assistant, inorganic fibers having an average particle diameter of 2 to 200 μm as a method for improving of the mechanical strength of a supported catalyst.

Patent Document 4 discloses a method of adding a silica sol and inorganic fibers. Patent Document 5 discloses a catalyst containing a scaly inorganic material having an average particle diameter of 10 μm to 2 mm and an average thickness of 0.005 to 0.3 times the average particle diameter. Patent Document 6 discloses a catalyst containing inorganic fibers having an acid amount of 0.05 mmol or less. It is mentioned that by controlling the acid amount of the inorganic fibers to 0.05 mmol or less, a catalyst of a high yield can be obtained.

BACKGROUND ART DOCUMENT

Patent Document

Patent Document 1: JP-A-2001-328951
Patent Document 2: JP-A-2002-273229
Patent Document 3: JP-A-H6-381
Patent Document 4: JP-A-H9-52053
Patent Document 5: JP-A-2007-000803
Patent Document 6: JP-A-2011-177616

SUMMARY OF INVENTION

Problem that Invention is to Solve

An object of the present invention is to provide a novel catalyst having high mechanical strength and capable of obtaining an unsaturated aldehyde or an unsaturated carboxylic acid in a high yield and a method for producing the same, and a method for producing an unsaturated aldehyde and/or an unsaturated carboxylic acid using the catalyst.

Means for Solving Problem

The present inventors made extensive and intensive investigations. As a result, they have found a novel catalyst having high mechanical strength by containing silane-treated glass fibers in a catalytic active component composed of molybdenum and bismuth as essential components, the catalyst being capable of obtaining an unsaturated aldehyde or an unsaturated carboxylic acid in a high yield, leading to accomplishment of the present invention.

Specifically, the present invention is concerned with the following.
(1) A catalyst for producing an unsaturated aldehyde and/or an unsaturated carboxylic acid, comprising:
  a compound containing a catalytic active component represented by the following formula (1); and
  silane-treated glass fibers:

$$Mo_a Bi_b Ni_c Co_d Fe_f X_g Y_h O_x \qquad (1)$$

(in the formula, Mo, Bi, Ni, Co and Fe represent molybdenum, bismuth, nickel, cobalt and iron, respectively; X means at least one element selected from tungsten, antimony, tin, zinc, chromium, manganese, magnesium, silica, aluminum, cerium and titanium; Y means at least one element selected from potassium, rubidium, thallium and cesium; a, b, c, d, f, g, h and x represent atomic numbers of molybdenum, bismuth, nickel, cobalt, iron, X, Y and oxygen, respectively;

a=12; b=0.1 to 7; c+d=0.5 to 20; f=0.5 to 8; g=0 to 2; h=0.005 to 2; and x is a value determined by oxidation states of the respective elements.)

(2) The catalyst as set forth above in (1),
wherein a content of the silane-treated glass fibers is in a range of 0.1% by mass to 30% by mass relative to the catalytic active component.

(3) The catalyst as set forth above in (1) or (2), which is prepared by physically mixing the compound containing the catalytic active component and the silane-treated glass fibers and supporting the mixture on an inert carrier.

(4) The catalyst as set forth above in any one of (1) to (3),
wherein when a calcining temperature is 510° C. or higher, an average catalyst particle diameter is 5.0 mm or more.

(5) The catalyst as set forth above in any one of (1) to (4),
wherein when a calcining temperature is 540° C. or higher, an average catalyst particle diameter is 6.0 mm or more.

(6) A method for producing the catalyst for producing an unsaturated aldehyde and/or an unsaturated carboxylic acid as set forth above in (1), comprising:
physically mixing the compound containing the catalytic active component represented by the formula (1) and the silane-treated glass fibers; and
supporting the mixture on an inert carrier.

(7) A method for producing an unsaturated aldehyde and/or an unsaturated carboxylic acid, which uses the catalyst as set forth above in any one of (1) to (5).

Effects of Invention

According to the catalyst of the present invention, high mechanical strength is revealed, and it is possible to obtain an unsaturated aldehyde or an unsaturated carboxylic acid in a high yield.

Mode for Carrying out Invention

The compound itself containing a catalytic active component which is used in the present invention can be prepared by a known method and is presented by the following formula (1):

$$Mo_aBi_bNi_cCo_dFe_fX_gY_hO_x \qquad (1)$$

(in the formula, Mo, Bi, Ni, Co and Fe represent molybdenum, bismuth, nickel, cobalt and iron, respectively; X means at least one element selected from tungsten, antimony, tin, zinc, chromium, manganese, magnesium, silica, aluminum, cerium and titanium; Y means at least one element selected from potassium, rubidium, thallium and cesium; a, b, c, d, f, g, h and x represent atomic numbers of molybdenum, bismuth, nickel, cobalt, iron, X, Y and oxygen, respectively; a=12; b=0.1 to 7, and preferably b=0.5 to 4; c+d=0.5 to 20, and more preferably c+d=1 to 12; f=0.5 to 8, and still more preferably f=0.5 to 5; g=0 to 2, and especially preferably g=0 to 1; h=0.005 to 2, and most preferably h=0.01 to 0.5; and x is a value determined by the oxidation states of the respective elements.)

Here, a powder of the compound containing a catalytic active component is prepared by a known method, such as a coprecipitation method, a spray drying method, etc. On that occasion, as raw materials to be used, nitrates, ammonium salts, hydroxides, oxides, acetate, and the like of various metal elements, such as molybdenum, bismuth, nickel, cobalt, iron, X, Y, etc., can be used without particular limitations. A powder of the compound containing catalytic active components of a different kind from each other can also be obtained by varying the kind and/or amount of the metal salt to be fed.

The thus obtained powder is calcined preferably at 200 to 600° C., and more preferably at 300 to 500° C. preferably under an air or nitrogen stream, whereby a preliminarily calcined powder can be obtained.

The thus obtained preliminarily calcined powder is shaped to prepare the catalyst of the present invention. The form of the shaped material is spherical, cylindrical or annular or the like and is not particularly limited, and the form should be selected taking into account the production efficiency or mechanical strength of the catalyst, or the like. However, the form is preferably spherical. On the occasion of shaping, it is general to carry out shaping by using a single preliminarily calcined powder. However, separately prepared granular preliminarily calcined powders having a different component formulation from each other may be previously mixed in an arbitrary proportion and shaped, or a method in which an operation of supporting a different preliminarily calcined powder on an inert carrier is repeated, whereby the preliminarily calcined powder is shaped in plural layers may also be adopted. It is to be noted that on the occasion of shaping, a shaping auxiliary agent, such as crystalline cellulose, etc., and silane-treated glass fibers are mixed. Use amounts of the shaping auxiliary agent and the silane-treated glass fibers are preferably 30% by weight or less, respectively relative to the catalytic active component. In addition, the shaping auxiliary agent and the silane-treated glass fibers may be previously mixed with the above-described preliminarily calcined powder prior to shaping, or may also be added in a shaping machine simultaneously with or before or after the addition of the preliminarily calcined powder.

Although the shaping method is not particularly limited, on the occasion of shaping in a cylindrical or annular form, a method of using a tablet shaping machine, an extrusion shaping machine, or the like is preferred. In the case of shaping in a spherical form, though the preliminarily calcined powder may be shaped in a spherical form by using a shaping machine, a method of supporting the preliminarily calcined powder on a carrier, such as an inert ceramic, etc., is preferred. In the case of using the silane-treated glass fibers and optionally other shaping auxiliary agent, they may be previously mixed with the preliminarily calcined powder and used, or they may also be separately added, respectively. Here, the supporting method is not particularly limited so long as it is a method in which the preliminarily calcined powder can be uniformly supported on the carrier, such as a tumbling granulation method, a method using a centrifugal flow coating apparatus, a wash coating method, etc. However, in the case of taking into account the production efficiency of the catalyst or the like, a method in which using an apparatus having a flat or uneven disk in a bottom of a fixed cylindrical vessel, a carrier charged within the vessel is vigorously agitated by means of rotation motion and revolution motion of the disk itself by rotating the disk at a high speed, and the preliminarily calcined powder and optionally a shaping auxiliary agent and a strength improver are added thereto, thereby supporting the powder components on the carrier is preferred.

It is to be noted that on the occasion of supporting, it is preferred to use a binder. Specific examples of the binder which can be used include water, ethanol, methanol, propanol, a polyhydric alcohol, polyvinyl alcohol that is a polymer-based binder, a silica sol aqueous solution that is an inorganic binder, and the like; ethanol, methanol, propanol, and a polyhydric alcohol are preferred; a diol, such as ethylene glycol, etc., a triol, such as glycerin, etc., and the like are preferred; and an aqueous solution of glycerin having a concentration of 5% by weight or more is preferred. By using an appropriate amount of a glycerin aqueous solution, the shaping properties become favorable, and a high-performance catalyst having high mechanical strength is obtained. A use amount of such a binder is typically 2 to 60 parts by weight based on 100 parts by weight of the preliminarily calcined powder, and in the case of a glycerin aqueous solution, its use amount is preferably 10 to 30 parts by weight. On the occasion of supporting, the binder and the preliminarily calcined powder may be alternately fed into a shaping machine, or they may be simultaneously fed.

Typically, as the inert carrier, one having an average particle diameter of about 3 to 10 mm is used, and the preliminarily calcined powder is supported thereon. A supporting amount thereof is determined taking into account conditions for using the catalyst, for example, a space velocity or a raw material hydrocarbon concentration. Although an average particle diameter of the catalyst having the preliminarily calcined powder supported on the inert carrier varies depending upon the supporting amount on the inert carrier, it is typically 4 to 11 mm.

It is to be noted that though a supporting rate of the preliminarily calcined powder (hereinafter referred to as "active powder") in a spherical supported catalyst is not particularly limited, it is typically 20 to 80% by weight. In the present invention, in the case of filling the preliminarily calcined powder in plurally divided catalyst layers as described below, a supporting rate (% by weight) of each of the catalyst layers, namely a supporting rate calculated by: [(weight of preliminarily calcined powder)/{(weight of preliminarily calcined powder)+(weight of inert carrier)+(weight of glass fibers)}]× 100, can be set to an appropriate value in view of the use.

It is preferred to again calcine the shaped catalyst prior to the use for the reaction. On the occasion of again calcining the shaped catalyst, a calcining temperature is typically 500 to 650° C.; and a calcining time is typically 3 to 30 hours, and preferably 4 to 15 hours, and it is properly set according to the reaction conditions to be used. In the case of providing plurally divided catalyst layers and filling the shaped catalyst in a reaction tube, as for the calcining temperature of the catalyst installed on the raw material gas inlet side, it is preferred to calcine the catalyst at a temperature higher than that of the catalyst on the gas outlet side regardless of its formulation, thereby controlling the activity. Although an atmosphere of the calcination may be either an air atmosphere or a nitrogen atmosphere, an air atmosphere is industrially preferred. Of these, the effects of the present invention are thoroughly exhibited with respect to catalysts having an average catalyst particle diameter of 5 mm or more and a calcining temperature of 510° C. or higher, and the effects are remarkably exhibited with respect to catalysts having an average catalyst particle diameter of 6 mm or more and a calcining temperature of 540° C. or higher.

The catalyst of the present invention can be used for the production of an unsaturated aldehyde and/or an unsaturated carboxylic acid. Specifically, the catalyst of the present invention can be used for a method of producing acrolein and acrylic acid by subjecting propylene to gas-phase catalytic oxidation with molecular oxygen or a molecular oxygen-containing gas; or a method of producing methacrolein and methacrylic acid by subjecting isobutylene and/or tertiary butyl alcohol to gas-phase catalytic oxidation with molecular oxygen or a molecular oxygen-containing gas. Above all, it is preferred to use the catalyst of the present invention for the production of acrolein and acrylic acid.

EXAMPLES

The present invention is explained in detail by reference to Examples and Comparative Examples. It is to be noted that the present invention is not limited to the following Examples so long as the gist of the present invention is not deviated. A propylene conversion and an effective yield are expressed by the following equations (1) and (2).

$$\text{Propylene conversion (mol \%)} = 100 \times [(\text{Molar number of reacted propylene})/(\text{Molar number of fed propylene})] \quad (1)$$

$$\text{Effective yield (mol \%)} = 100 \times [\{(\text{Molar number of produced acrolein})+(\text{Molar number of produced acrylic acid})\}/(\text{Molar number of fed propylene})] \quad (2)$$

The strength of the catalyst to be used for the reaction is very important from the viewpoint of practical use. The strength of the catalysts used in the Examples was evaluated in terms of an attrition resistance determined by the following method.

A cylindrical rotating machine having a radius of 14 cm and having one sheet of baffle provided therein was charged with 50 g of the obtained catalyst and rotated at 23 rpm for 10 minutes. Thereafter, an exfoliated powder was removed by a sieve, and a residual amount was measured. A proportion of the exfoliated powder was calculated according to the following equation (3), and this value is hereinafter expressed as the attrition resistance. When the attrition resistance is smaller, the strength becomes higher, and such is preferred. From the standpoint of practical use, the attrition resistance is preferably 3% by weight or less, and more preferably 1% by weight or less.

$$\text{Attrition resistance (wt \%)} = 100 \times [\{(\text{Sample weight}) - (\text{Sample weight remaining on the sieve})\}/(\text{Sample weight})] \quad (3)$$

The average particle diameter of the catalyst was measured by the following method.

100 granules of the spherical catalyst were randomly collected and measured for the diameter by using calipers. An average value of the obtained data was defined as the average particle diameter of the catalyst.

Example 1

(Preparation of Catalyst)

789.0 parts by weight of ammonium molybdate and 4.4 parts by weight of potassium nitrate were dissolved in 3,000 parts by weight of distilled water while heating and stirring, thereby obtaining an aqueous solution (A). Separately, 563.8 parts by weight of cobalt nitrate, 303.2 parts by weight of nickel nitrate, and 263.3 parts by weight of ferric nitrate were dissolved in 1,000 parts by weight of distilled water, thereby preparing an aqueous solution (B); and 301.7 parts by weight of bismuth nitrate was dissolved in 300 parts by weight of distilled water which had been made acidic by the addition of 77 parts by weight of 60% concentrated nitric acid, thereby preparing an aqueous solution (C). The above-described aqueous solution (A) was successively mixed with the above-described aqueous solutions (B) and (C) while vigorously stirring, and the produced suspension was dried by a spray dryer and calcined at 440° C. for 6 hours, thereby obtaining a preliminarily calcined powder. At this time, a formulation ratio of the catalytic active component excluding oxygen was Mo=12, Bi=1.7, Ni=2.8, Fe=1.8, Co=5.2, and K=0.12 in terms of an atomic ratio.

Thereafter, a mixed powder of 100 parts by weight of the preliminarily calcined powder, 5 parts by weight of crystalline cellulose, and 3 parts by weight of MILLED FIBER EFH150_31 (silane-treated), manufactured by Central Glass Co., Ltd. was added to 97 parts by weight of an inert carrier (a spherical material composed mainly of alumina and silica and having an average diameter of 6.0 mm) by using a 20% by weight glycerin aqueous solution as a binder, and the resultant was supported and shaped. The obtained catalyst was calcined at 540° C. for 4 hours in an air atmosphere by using a box-type hot-air calcining furnace, thereby obtaining a catalyst (D) of the present invention. An attrition resistance of the obtained catalyst is described in the following Table 1. An average particle diameter of the shaped catalyst (D) was 6.9 mm.

(Oxidation Reaction Test)

In a stainless steel-made reaction vessel having an inner diameter of 28.4 mm, silica-alumina spheres having an average diameter of 4.0 mm were successively filled in a length of 2 cm from the raw material gas inlet side; furthermore, the above-described shaped catalyst and silica-alumina spheres having an average diameter of 4.0 mm were filled in a length of 15 cm and 37 cm, respectively; and the resulting reaction vessel was set in a fluidized bath whose reaction bath temperature had been made constant at 320° C. by using alumina sand. A gas in which feed amounts of propylene, air, and water had been set in a raw material molar ratio of propylene/oxygen/water/nitrogen of 1/1.7/3/6.4 was introduced at a space velocity of 630 h$^{-1}$ into the oxidation reaction vessel, and after starting the reaction, the temperature was raised to 350° C. and kept for 12 hours (this treatment is referred to as "high-temperature reaction treatment") and then decreased to 330° C., followed by carrying out quantitative determination. The same oxidation reaction test was repeated four times, and average values of the resulting propylene conversion and effective yield are described in Table 1.

Comparative Example 1

A shaped catalyst (E) for comparison was prepared under the same conditions as those in Example 1, except that the EFH150_31 was not added, and that the amount of the inert carrier was changed to 100 parts by weight, and then subjected to the oxidation reaction test and attrition resistance measurement. Results are shown in Table 1. An average particle diameter of the shaped catalyst (E) was 6.9 mm.

Comparative Example 2

A shaped catalyst (F) for comparison was prepared under the same conditions as those in Example 1, except that EFH150_01 (non-silane-treated glass fibers), manufactured by Central Glass Co., Ltd. was used in place of the EFH150_31, and then subjected to the oxidation reaction test and attrition resistance measurement. Results are shown in Table 1. An average particle diameter of the shaped catalyst (F) was 6.9 mm.

TABLE 1

Propylene oxidation reaction results and strength measurement results

|  | Propylene conversion (mol %) | Effective yield (mol %) | Attrition resistance (wt %) |
|---|---|---|---|
| Example 1 | 96.1 | 90.5 | 0.3 |
| Comparative Example 1 | 96.1 | 90.5 | 4.2 |
| Comparative Example 2 | 95.9 | 90.1 | 0.2 |

It is noted from Comparative Example 1 that in the case of not using the silane-treated glass fibers, the attrition resistance becomes very large, so that the catalyst strength is insufficient. In addition, it is noted from Comparative Example 2 that in the case of using the non-silane-treated glass fibers as the shaping auxiliary agent, though the attrition resistance is improved, the effective yield is lowered. It was confirmed from Example 1 and Comparative Example 1 that by using the silane-treated glass fibers as the shaping auxiliary agent, the attrition resistance is improved without causing a lowering of the catalytic performance.

Example 2

(Preparation of Catalyst)

A catalyst (G) of the present invention was obtained under the same conditions as those in Example 1, except that a supported shaped catalyst was calcined at a temperature of 550° C. for 4 hours in an air atmosphere by using a tunnel-type hot-air calcining furnace. An attrition resistance of the obtained catalyst is described in the following Table 2. An average particle diameter of the shaped catalyst (G) was 7.1 mm.

789.0 parts by weight of ammonium molybdate and 3.5 parts by weight of potassium nitrate were dissolved in 3,000 parts by weight of distilled water while heating and stirring, thereby obtaining an aqueous solution (H). Separately, 563.8 parts by weight of cobalt nitrate, 303.2 parts by weight of nickel nitrate, and 263.3 parts by weight of ferric nitrate were dissolved in 1,000 parts by weight of distilled water, thereby preparing an aqueous solution (I); and 301.7 parts by weight of bismuth nitrate was dissolved in 300 parts by weight of distilled water which had been made acidic by the addition of 77 parts by weight of 60% concentrated nitric acid, thereby preparing an aqueous solution (J). The above-described aqueous solution (H) was successively mixed with the above-described aqueous solutions (I) and (J) while vigorously stirring, and the produced suspension was dried by a spray dryer and calcined at 440° C. for 6 hours, thereby obtaining a preliminarily calcined powder. At this time, a formulation ratio of the catalytic active component excluding oxygen was Mo=12, Bi=1.7, Ni=2.8, Fe=1.8, Co=5.2, and K=0.1 in terms of an atomic ratio.

Thereafter, a mixed powder of 100 parts by weight of the preliminarily calcined powder and 5 parts by weight of crystalline cellulose was added to 100 parts by weight of an inert carrier (a spherical material composed mainly of alumina and silica and having an average diameter of 4.0 mm) by using a 20% by weight glycerin aqueous solution as a binder, and the resultant was supported and shaped. The obtained catalyst was calcined at 530° C. for 4 hours in an air atmosphere by using a tunnel-type hot-air calcining furnace, thereby obtaining a catalyst (K) of the present invention.

(Oxidation Reaction Test)

In a stainless steel-made reaction vessel having an inner diameter of 27.2 mm, in which a jacket for circulating a molten salt as a heat medium and a thermocouple for measuring a catalyst layer temperature were installed in a tube axis, silica-alumina spheres having an average diameter of 5.2 mm, the oxidation catalyst (G) as an oxidation catalyst layer first layer (raw material gas inlet side), and the oxidation catalyst (K) as an oxidation catalyst layer second layer (gas outlet side) were successively filled in a length of 15 cm, 80 cm, and 215 cm, respectively from the raw material gas inlet side thereof, and a reaction bath temperature was set to 330° C. A gas in which feed amounts of propylene, oxygen, water, and nitrogen had been set in a raw material molar ratio of propylene/oxygen/water/nitrogen of 1/1.75/2.0/10 was introduced at a space velocity of 1,470 h$^{-1}$ into the oxidation reaction vessel, and an outlet pressure of the reaction vessel was set to 50 kPaG. After starting the reaction, at the time of elapsing 300 hours, a test of varying the reaction temperature at intervals of 3° C. was carried out such that a total yield of acrolein and acrylic acid became a maximum, thereby determining a maximum effective yield. In addition, a maximum temperature (peak temperature) within the catalyst layer was measured by using a thermocouple. Results are shown in the following Table 2.

Comparative Example 3

(Preparation of Catalyst)

A catalyst (L) for comparison was obtained under the same conditions as those in Comparative Example 1, except that a supported shaped catalyst was calcined at a temperature of 550° C. for 4 hours in an air atmosphere by using a tunnel-type hot-air calcining furnace. An attrition resistance of the obtained catalyst is described in Table 2. An average particle diameter of the catalyst (L) was 7.1 mm.

(Oxidation Reaction Test)

The test of varying the reaction temperature was carried out under the same conditions as those in Example 2, except that the oxidation catalyst (L) was used as the oxidation catalyst layer first layer (raw material gas inlet side). Results obtained are shown in Table 2.

TABLE 2

Propylene oxidation reaction results and catalyst strength test results

| | Reaction temperature (° C.) | Peak temperature (° C.) | Effective yield (mol %) | Attrition resistance (wt %) |
|---|---|---|---|---|
| Example 2 | 333 | 402 | 92.1 | 0.3 |
| Comparative Example 3 | 333 | 405 | 91.7 | 1.2 |

It was confirmed from Example 2 and Comparative Example 3 that even on the occasion of using the catalyst containing silane-treated glass fibers in combination with other catalyst, the effective yield is not lowered as compared with the time of using a catalyst not containing the silane-treated glass fibers.

While the invention has been described in detail and with reference to specific embodiments thereof, it will be apparent to one skilled in the art that various changes and modifications can be made therein without departing from the spirit and scope thereof.

It is to be noted that the present application is based on a Japanese patent application filed on Apr. 25, 2013 (Japanese Patent Application No. 2013-092005), the entireties of which are incorporated by reference. In addition, all references cited herein are incorporated as a whole.

INDUSTRIAL APPLICABILITY

The catalyst of the present invention is useful for the production of an unsaturated aldehyde and/or an unsaturated carboxylic acid.

The invention claimed is:

1. A catalyst for producing an unsaturated aldehyde and/or an unsaturated carboxylic acid, comprising:
    a compound containing a catalytic active component having the following formula (1); and
    silane-treated glass fibers:

$$Mo_aBi_bNi_cCo_dFe_fX_gY_hO_x \qquad (1)$$

wherein Mo, Bi, Ni, Co and Fe represent molybdenum, bismuth, nickel, cobalt and iron, respectively; X means one or more elements selected from the group consisting of tungsten, antimony, tin, zinc, chromium, manganese, magnesium, silica, aluminum, cerium and titanium; Y means one or more elements selected from the group consisting of potassium, rubidium, thallium and cesium; a, b, c, d, f, g, h and x represent atomic numbers of molybdenum, bismuth, nickel, cobalt, iron, X, Y and oxygen, respectively; a=12; b=0.1 to 7; c+d=0.5 to 20; f=0.5 to 8; g=0 to 2; h=0.005 to 2; and x is a value determined by oxidation states of the respective elements.

2. The catalyst according to claim 1,
    wherein the content of the silane-treated glass fibers is in a range of 0.1% by mass to 30% by mass relative to the catalytic active component.

3. The catalyst according to claim 1, which is prepared by physically mixing the compound containing the catalytic active component and the silane-treated glass fibers and supporting the mixture on an inert carrier.

4. The catalyst according to claim 1,
    wherein said catalyst has an average catalyst particle diameter of 5.0 mm or more after calcination at a temperature of 510° C. or higher.

5. The catalyst according to claim 1,
    wherein said catalyst has an average catalyst particle diameter of 6.0 mm or more after calcination at a temperature of 540° C. or higher.

6. A method for producing the catalyst for producing an unsaturated aldehyde and/or an unsaturated carboxylic acid according to claim 1, comprising:
    physically mixing the compound containing the catalytic active component having the formula (1) and the silane-treated glass fibers; and
    supporting the mixture on an inert carrier.

7. A method for producing an unsaturated aldehyde and/or an unsaturated carboxylic acid by subjecting propylene, or isobutylene and/or tertiary butyl alcohol, to a gas-phase catalytic oxidation with molecular oxygen or a molecular oxygen-containing gas in the presence of a catalyst according to claim 1.

* * * * *